(12) United States Patent
Folse et al.

(10) Patent No.: US 10,583,257 B2
(45) Date of Patent: Mar. 10, 2020

(54) METHOD AND APPARATUS FOR CONTROLLING THE DISCHARGE RATE OF A SYRINGE

(71) Applicant: BREEZZANGEL, LLC, New Orleans, LA (US)

(72) Inventors: Gregory Folse, Covington, LA (US); Tonia Dandry Aiken, New Orleans, LA (US); James Beam Aiken, New Orleans, LA (US); Tina Dandry Mayes, Marrero, LA (US)

(*) Notice: Subject to any disclaimer, the term of this patent is extended or adjusted under 35 U.S.C. 154(b) by 621 days.

(21) Appl. No.: 14/754,806

(22) Filed: Jun. 30, 2015

(65) Prior Publication Data

US 2015/0374923 A1 Dec. 31, 2015

Related U.S. Application Data

(60) Provisional application No. 62/018,740, filed on Jun. 30, 2014.

(51) Int. Cl.
*A61M 5/315* (2006.01)

(52) U.S. Cl.
CPC .... *A61M 5/31515* (2013.01); *A61M 5/31513* (2013.01); *A61M 5/31525* (2013.01); *A61M 5/31573* (2013.01); *A61M 2005/3152* (2013.01); *A61M 2005/31523* (2013.01)

(58) Field of Classification Search
CPC ......................... A61M 5/31515; A61J 1/2096
See application file for complete search history.

(56) References Cited

U.S. PATENT DOCUMENTS

| | | | | |
|---|---|---|---|---|
| 3,680,558 A | * | 8/1972 | Kapelowitz | A61B 5/15003 604/89 |
| 3,875,979 A | * | 4/1975 | Hults | A61M 5/1782 141/27 |
| 4,502,488 A | * | 3/1985 | Degironimo | A61B 5/028 600/505 |
| 4,561,856 A | * | 12/1985 | Cochran | A61M 5/155 604/143 |
| 4,652,261 A | * | 3/1987 | Mech | A61D 7/00 119/859 |
| 4,690,154 A | * | 9/1987 | Woodford | A61M 5/31511 600/578 |
| 4,744,786 A | * | 5/1988 | Hooven | A61M 5/155 128/DIG. 12 |
| 5,356,375 A | * | 10/1994 | Higley | A61M 5/36 604/142 |
| 5,431,645 A | * | 7/1995 | Smith | A61B 18/1445 606/1 |

(Continued)

*Primary Examiner* — Bhisma Mehta
*Assistant Examiner* — Matthew A Engel
(74) *Attorney, Agent, or Firm* — Ted M. Anthony

(57) ABSTRACT

A method and apparatus for use in controlling a dispensing rate of medication or other substance via a syringe, including, without limitation, into a patient, intravenous line port or heparin lock. A force (typically manual) is applied to an input plunger of a dashpot, which is directly coupled to a piston which, in turn, is coupled to an output plunger. The force applied to the input plunger is buffered and transmitted to the output plunger. The output plunger acts upon the plunger of a conventional syringe, thereby resulting in flow of medicine or any other substance from the syringe at a desired and controlled flow rate.

5 Claims, 13 Drawing Sheets

(56) References Cited

U.S. PATENT DOCUMENTS

| | | | | |
|---|---|---|---|---|
| 5,569,189 A * | 10/1996 | Parsons | A61M 5/1782 | 604/22 |
| 5,795,337 A * | 8/1998 | Grimard | A61M 5/31511 | 604/222 |
| 5,810,398 A * | 9/1998 | Matkovich | A61M 39/1011 | 285/3 |
| 6,306,125 B1 * | 10/2001 | Parker | A61F 2/02 | 604/117 |
| 6,536,805 B2 * | 3/2003 | Matkovich | A61M 39/1011 | 285/3 |
| 7,195,623 B2 * | 3/2007 | Burroughs | A61J 1/2096 | 604/187 |
| 8,007,475 B2 * | 8/2011 | Kosinski | A61M 5/31511 | 604/191 |
| 8,231,567 B2 * | 7/2012 | Tennican | A61J 1/2096 | 604/89 |
| 9,114,216 B2 * | 8/2015 | Sutkin | A61M 5/31526 | |
| 9,452,261 B2 * | 9/2016 | Alon | A61M 5/20 | |
| 9,751,056 B2 * | 9/2017 | McArthur | B01F 13/0023 | |
| 2002/0093192 A1 * | 7/2002 | Matkovich | A61M 39/1011 | 285/3 |
| 2007/0179452 A1 * | 8/2007 | Kosinski | A61M 5/31511 | 604/218 |
| 2007/0233038 A1 * | 10/2007 | Pruitt | A61M 5/31586 | 604/522 |
| 2007/0249996 A1 * | 10/2007 | Tennican | A61J 1/2096 | 604/93.01 |
| 2008/0319422 A1 * | 12/2008 | Cardenas | A61B 17/3401 | 604/537 |
| 2009/0118680 A1 * | 5/2009 | Goldbrunner | A61M 5/2053 | 604/236 |
| 2011/0224610 A1 * | 9/2011 | Lum | A61M 5/38 | 604/125 |
| 2012/0209111 A1 * | 8/2012 | Cowan | A61M 5/007 | 600/432 |
| 2014/0174596 A1 * | 6/2014 | Lopez | A61J 1/2096 | 141/10 |
| 2017/0326293 A1 * | 11/2017 | Sims | A61M 5/1456 | |

\* cited by examiner

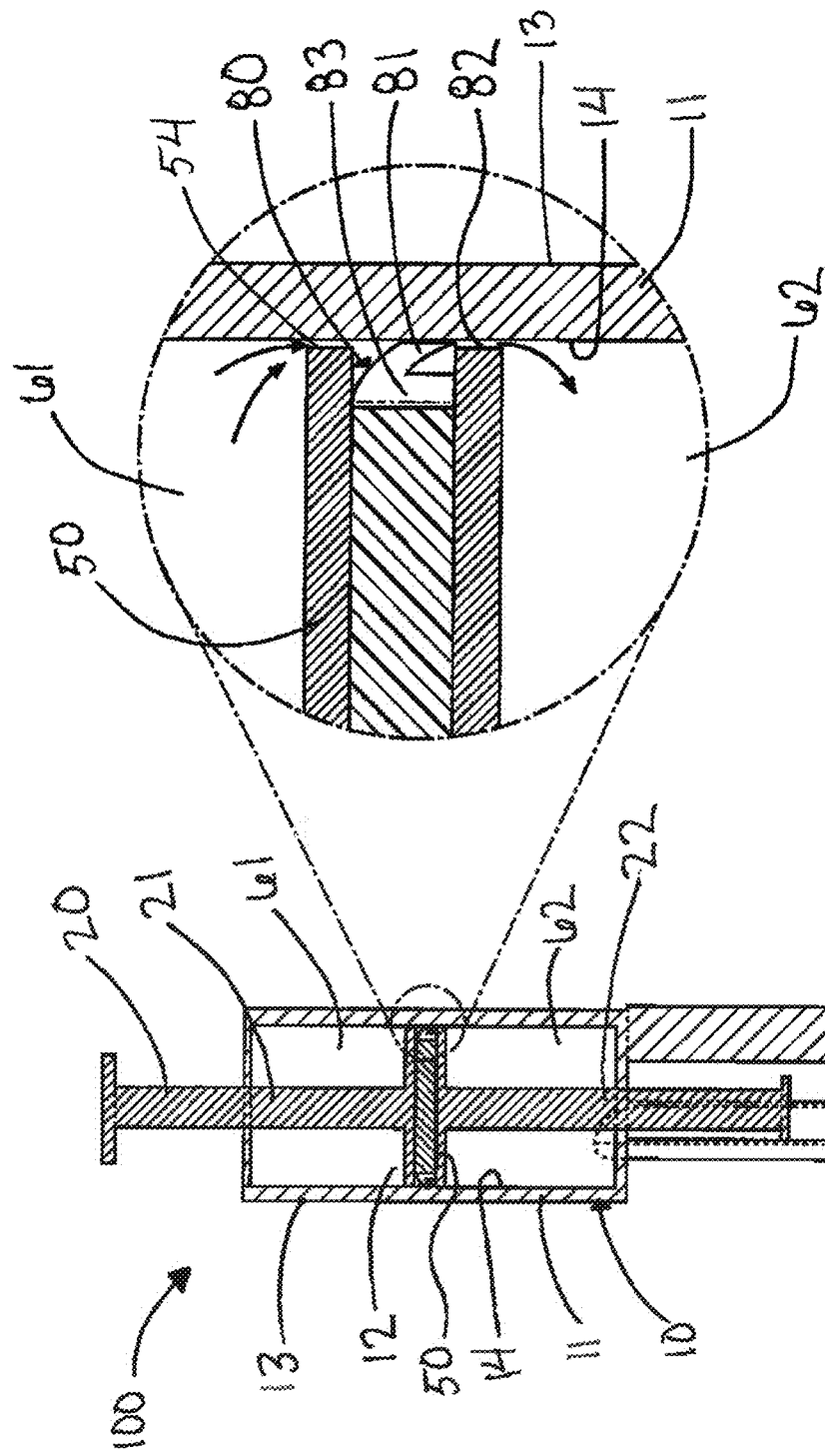

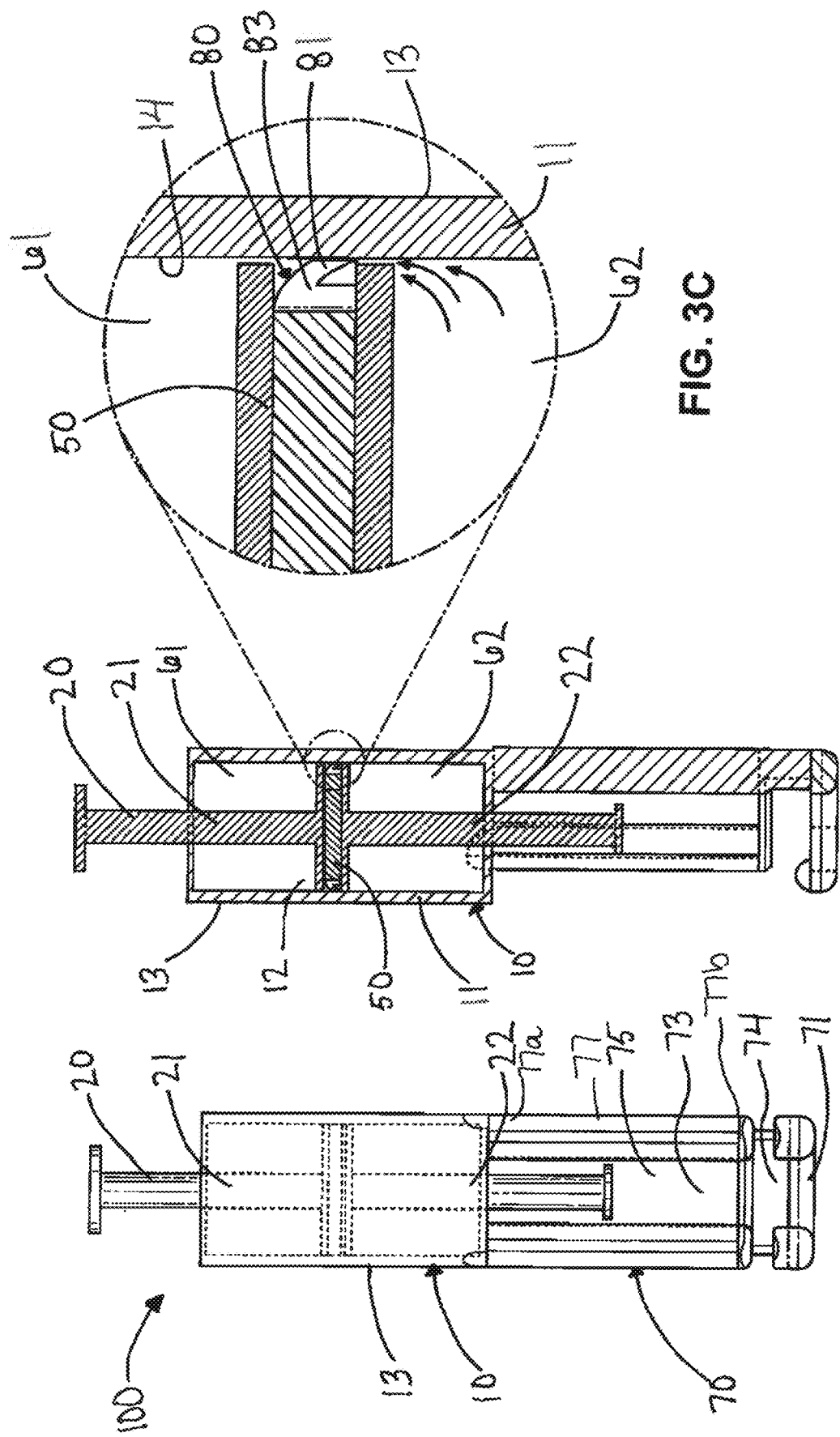

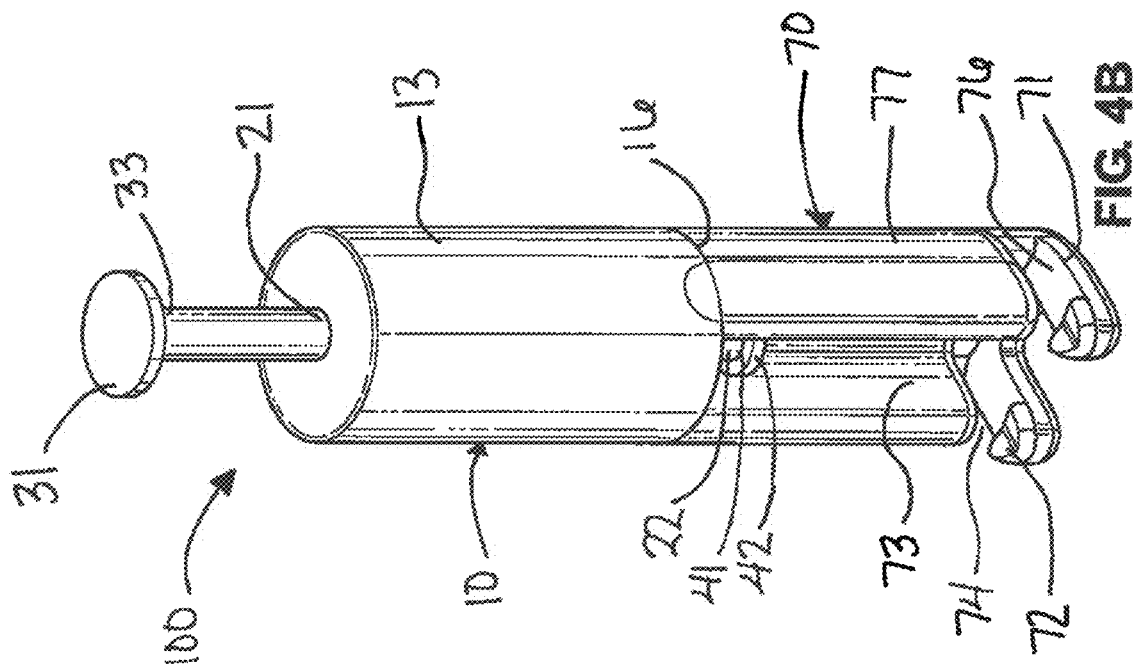
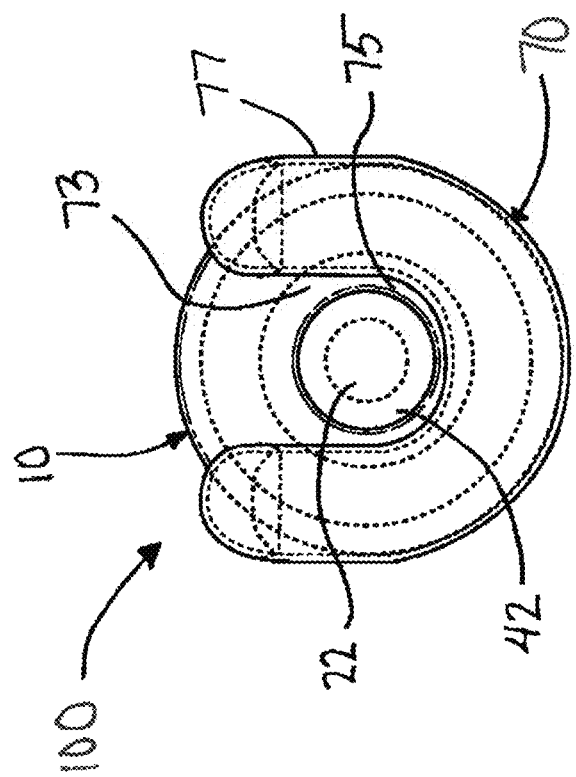

| MEDICATION | COMMENT | CONCENTRAT | PER | DOSE | VALUE 1 | DOSE / H | UNIT |
|---|---|---|---|---|---|---|---|
| Ketamine | | 100 mg | ml | | | | |
| Zofran | | 2 mg | ml | 0.15 mg | kg (max 16 mg) | | |
| Ketamine | | 50 mg | ml | (www.drugs.com) | | | |
| Promethazine | | 25 mg | ml | 25 mg | | 1 | min |
| Labetolol | early MI treatment | 5 mg | ml | 20 mg | | 2 | min |
| Atenolol | | 0.5 mg | ml | 5 mg | | 5 | min |
| Diltiazem | PSVT | 5 mg | ml | 0.25 mg | kg | 2 | min |
| Furosemide | | 10 mg | ml | 4 mg max | | 4 mg | min |
| Lidocaine | | 100 mg | 5 ml | 1-1.5 mg | kg | 2 to 3 | min |
| Diltiazem | | 5 mg | ml | 0.35 mg | kg | | 2 min |
| Propranolol | e-threatening arrhythmia | 1 mg | ml | 1 to 3 mg | | 1 to 3 | min |
| Esmolol | (Brevibloc) for SVT | 10 mg | ml | 500 mcg | kg | | 1 min |
| Ketamine | | 10 mg | ml | 0.5 mg | kg | | 1 min |
| Lidocaine | | 100 mg | 5 ml | | | | |
| Metoprolol | (early MI treatment | 1 mg | ml | 5 mg | | 1 | min (q 3 min x 3) |
| Amidate | | 2 mg | ml | 0.3 mg | kg | 30-60 | sec |

| COMMENT | DOSE / UNIT | | ml / min |
|---|---|---|---|
| | | | 0.34 |
| Adult (above 40 kg) dose 4 mg | 4 | mg | 0.5 |
| for 5-10 minutes of anesthesia | | | 0.68 |
| | 25 | mg | 1 |
| | 10 | mg | 2 |
| | 5 | mg | 2 |
| Usual does 20 mg (calc does for lower wt | 20 | mg | 2 |
| | 4 | mg | 2.5 |
| Average 50-100 mg | 50 | mg | 2.5 |
| Usual does 25 mg (calc does for lower wt | 25 | mg | 2.5 |
| | 1 | mg | 3 |
| 150 lb pt=68 kg=34090 mcg=34 mg | 34 | mg | 3.4 |
| 150 lb pt=68 kg=34 mg/kg/min | 34 | mg | 3.4 |
| May repeat in 3-5 min, max 3 doses | 100 | mg | 5 |
| | 5 | mg | 5 |
| 150 lb pt=10.4 mg to be delivered | 10.2 | mg | 5.1 |

FIG. 10 (Cont')

From FIG. 10

METHOD AND APPARATUS FOR CONTROLLING THE DISCHARGE RATE OF A SYRINGE

CROSS REFERENCES TO RELATED APPLICATION

Priority of U.S. Provisional Patent Application Ser. No. 62/018,740, filed Jun. 30, 2014, incorporated herein by reference, is hereby claimed.

STATEMENTS AS TO THE RIGHTS TO THE INVENTION MADE UNDER FEDERALLY SPONSORED RESEARCH AND DEVELOPMENT

None

BACKGROUND OF THE INVENTION

1. Field of the Invention

The present invention pertains to a method and apparatus for controlling a dispensing rate of fluid (such as, for example, liquid medication) via a syringe, including, without limitation, into an intravenous (IV) line port. More particularly, the present invention pertains to a method and apparatus for regulating the rate of infusion of certain drugs and medications into a patient.

2. Brief Description of the Prior Art

Conventional syringes are well known. Although specific design parameters can vary, in most instances such syringes generally comprise a substantially hollow tube or "barrel" having a proximate end and a distal end. Said barrel defines an inner chamber defining an internal space. A moveable plunger member is received within an opening at said proximate end of said barrel, and is slidably disposed within said barrel. An outlet port or opening is formed at the distal end of said barrel (to which a hollow hypodermic needle or other fixture can be operationally attached).

When dispensing of fluid from such a syringe is desired, a predetermined volume of such fluid is first loaded within the inner space of said barrel. Thereafter, axial force is applied to said plunger, causing it to move into said inner space of said barrel. Said plunger displaces said fluid from the inner space of said barrel, forcing the fluid out of the outlet port of said barrel.

Unfortunately, dispensing of fluid from such conventional syringes can be imprecise and, in some cases, dangerous. It can often be difficult for a user to apply constant pressure to a syringe plunger, which can result in inconsistent output flow rates from a conventional syringe. This can be particularly dangerous or problematic when such a syringe is being used to inject medicine or other substance into a person. In such cases, inconsistent or erratic infusion rates (i.e., infusion that is too fast, too slow, or both), can cause injury or death to a person.

Pump systems exist to provide substantially constant infusion rates. However, many of these systems are incompatible with existing conventional syringes. Further, such existing systems are typically expensive, complicated, difficult to use and not conveniently portable.

Thus, there is a need for a simple, inexpensive and portable system that can be used with conventional syringes to ensure consistent and predicable output rate for fluid(s) being dispensed from such syringes.

SUMMARY OF THE INVENTION

The present invention comprises a primary application for controlling a dispensing rate of medication via syringe, including, without limitation, into an intravenous line port or heparin lock. In a preferred embodiment, a user of the apparatus of the present invention applies a force (typically manual) to an input plunger of a dashpot, which is directly coupled to a piston, wherein said piston is further directly coupled to an output plunger. All forces are imparted substantially along a single axis.

The piston divides a cylindrical area into a plurality of chambers (typically two, although more are possible): an upper chamber and a lower chamber. The upper chamber and lower chamber communicate via a transfer tube of fixed diameter and length through the piston. The upper chamber is sealed, except for the transfer tube. By way of illustration, but not limitation, the lower chamber may be open to the atmosphere if air is used as a medium; however, the lower chamber may be sealed if another fluid is used as a transfer medium.

By orienting the linear motions of the device along a "Y" axis, the motions of the piston can be described as down or deploying, and up or retracting. Applying a positive force to the input plunger causes the piston to move in a relatively downward direction, thereby increasing the volume of the upper chamber. This volumetric change results in a reduction of pressure in the upper chamber. When the negative pressure in the upper chamber head space reaches equilibrium with the applied input pressure, the linear motion of the piston/plunger assembly stalls. The flow of a medium from one embodiment to another through the transfer tube prevents stalling and allows the downward linear motion of the piston to continue at a rate that is described by Poisuelle's law, under the stipulation that the flow remains laminar.

In a preferred embodiment, the input pressure that would cause an unregulated syringe plunger to travel a particular distance in a particular period of time can be buffered to take practically any desired length of time, depending on the diameter and length of the transfer tube and the dynamic viscosity of fluid flowing through said transfer tube. This buffering reduces the linear rate of travel, thereby preventing a user (such as, for example, a health care provider) from injecting medication into a patient at a too rapid rate, which can cause physical damage, or death, to the patient.

In a preferred embodiment, the apparatus of the present invention is beneficially interjected between a user's manual application of force and the input plunger of a syringe, thereby smoothing out the resultant pressure applied to said plunger, and thus controlling the volume of fluid discharge from said syringe. The device of the present invention employs a controlled transfer of a medium from one chamber to another through a fixed diameter transfer tube to control a maximum effective rate of linear travel of a plunger and piston over a specified range of input pressures. Said linear plunger travel rate is directly proportional to a syringe liquid discharge flow rate.

Because applied pressure is so relatively low, air flow should remain substantially laminar and, thus, Poisuelle's law would apply with some modifications for compressible fluids. For more precise travel rates, the medium fluid can instead comprise a liquid of having greater dynamic viscosity than air; by way of illustration, but not limitation, such liquid can comprise, for example, glycerol (typically having viscosity of approximately 1.4 Pa·s) or propylene glycol (typically having viscosity of approximately 0.04 Pa·s). The lack of compressibility of such liquid eliminates any compressive surge that may be observed when using a gas as a medium. Moreover, selection of a fluid according to its dynamic viscosity gives a differing rate of transfer with a same transfer tube dimension and, thus, allows for adjustability of the present invention by using a fluid having a different dynamic viscosity.

The linear rate of travel, and the subsequent flow rate, can be effectively increased or decreased by varying one or more of the following: (1) the diameter of the transfer tube; (2) the length of the transfer tube; (3) the dynamic viscosity of the fluid; (4) the volume of the upper or lower chambers; (5) the syringe size (which will alter the flow rate); or, (6) the applied input pressure. The impact of fluid temperature and turbulent flow is of very small or negligible consequence in a preferred embodiment of the present invention.

In a preferred embodiment, the fluid pressure sealing method between the chambers of the present invention may comprise an O-ring, a directional radial lip seal, a deposition of material such as overmolding, an interference fit, or another suitable method.

In a preferred embodiment, the device of the present invention is compatible with conventional disposable syringes that are readily available in the medical environment. The flange of the syringe, usually held between the index and the second fingers for dispensing, is placed into an open clevis, either recessed and open or flat with a retaining spring, to hold the syringe in a proper orientation to the piston and plunger assembly, thereby maintaining axial alignment while the buffering device is operated. The output plunger of the device pushes against the input plunger of the syringe. Pre-filled syringes (such as, for example, pre-filled syringes marketed under the registered mark "Abboject"®) can be pre-loaded into the device of the present invention and placed in a dispensary or on emergency department carts for quick deployment and use when a need arises. Devices with relative clevis dimensions can be available to combine with the common sizes of syringes used with high alert medications.

For syringes that are filled at the instruction of a provider, a collapsible radial lip seal can act as the sealing method of the piston to the cylinder wall. Such a sealing method allows the device input plunger to be retracted at a rapid rate in the reverse direction, but it would resume full buffering in the normal dispensing direction. Without the collapsible radial lip seal, meaning equal sealing ability in either direction, the time to retract the plunger upwards is similar to the time to deploy the plunger downwards, i.e., for the same pressure applied across the total possible travel distance with identical upper and lower chambers.

In an alternative embodiment, a method of retraction can use a floating check ball that acts as a one-way or check valve in the piston, wherein the density of the ball is beneficially similar to the density of the fluid. Alternatively, for best reliability and accuracy of check ball to piston sealing, check ball materials that vary significantly from the fluid density may be utilized if the check ball is back seated with a suitable coiled compression spring.

When the piston is retracted, an influx of the fluid through a valve port will move the ball off of a seat and into a retainer, while the fluid then flows around said ball through a relief port. This allows for a rapid retraction of the piston. When the piston has been sufficiently retracted in order to properly fit the syringe into the clevis, the motion of the piston is then reversed, thereby pushing the fluid up through the check valve port and then bringing the check ball with it until the ball finds a home position against the seat. Thereafter, the piston motion is regulated by the variables in Poisuelle's equations, as long as there is constant pressure on the piston.

BRIEF DESCRIPTION OF THE DRAWINGS/FIGURES

The foregoing summary, as well as any detailed description of the preferred embodiments, is better understood when read in conjunction with the drawings and figures contained herein. For the purpose of illustrating the invention, the drawings and figures show certain preferred embodiments. It is understood, however, that the invention is not limited to the specific methods and devices disclosed in such drawings or figures.

FIG. 2A depicts a side, longitudinal sectional view of a preferred embodiment of a syringe apparatus of the present invention.

FIG. 2B depicts a detailed view of a highlighted portion of piston member comprising a radial lip seal of the present invention.

FIG. 3A depicts a front view of a preferred embodiment of a syringe apparatus of the present invention.

FIG. 3B depicts a side, longitudinal sectional view of a preferred embodiment of a syringe apparatus of the present invention.

FIG. 3C depicts a detailed view of a highlighted portion of piston member comprising a radial lip seal of the present invention.

FIG. 4A depicts a bottom view of a preferred embodiment of a syringe apparatus of the present invention.

FIG. 4B depicts a side perspective view of a preferred embodiment of a syringe apparatus of the present invention.

FIG. 10 depicts a tabular chart depicting a variety of medications and concentrations thereof with proposed injection rates.

DETAILED DESCRIPTION OF A PREFERRED EMBODIMENT

Figure 1:
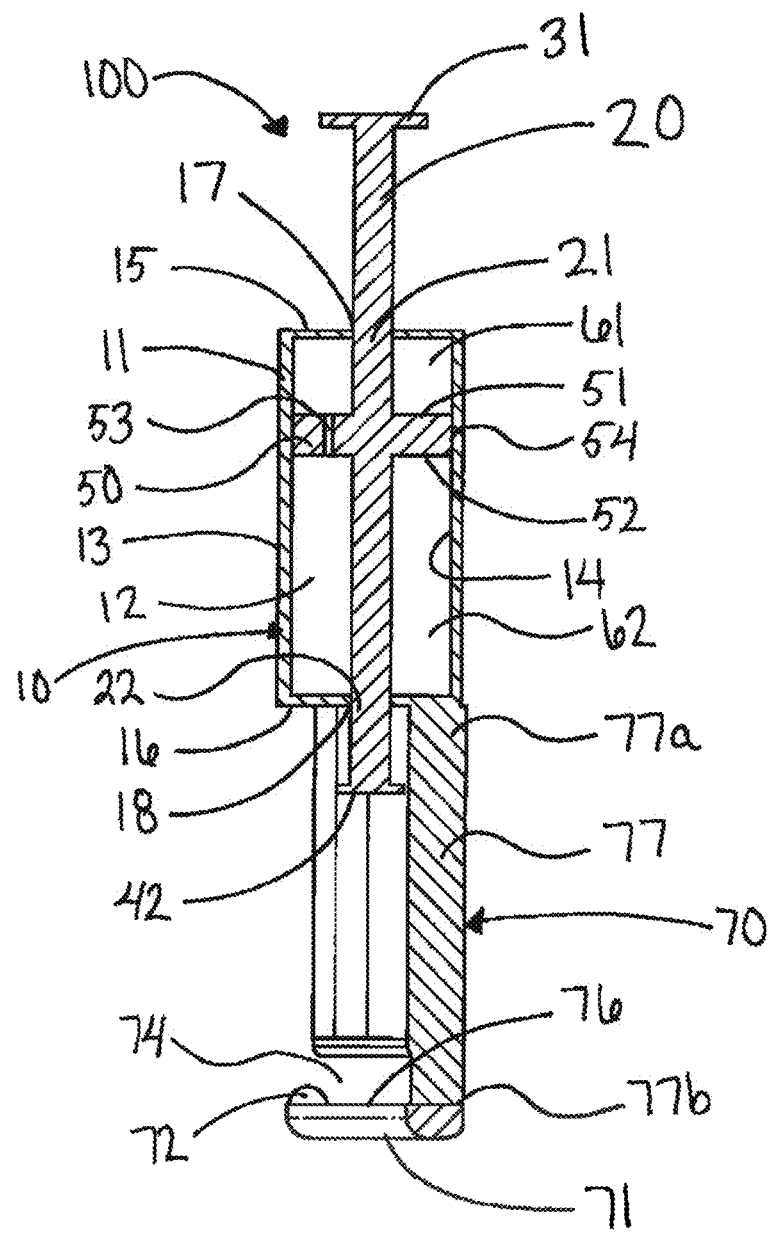
FIG. 1 depicts a side, longitudinal sectional view of a preferred embodiment of a syringe apparatus of the present invention.

Referring to the drawings, FIG. 1 depicts a side, longitudinal sectional view of a preferred embodiment of a dispensing assembly 100 of the present invention generally comprising a dashpot assembly 10 attachably coupled to a clevis bracket assembly 70.

In a preferred embodiment, dashpot assembly 10 generally comprises substantially cylindrical housing 13 having top member 15, base member 16 and side wall 11 that collectively cooperate to define an inner cavity, or chamber 12, formed within said housing 13. Side wall 11 defines inner surface 14. An upper aperture 17 extends through top member 15, while a lower aperture 18 extends through base member 16.

Still referring to FIG. 1, plunger member 20 generally comprises input plunger rod section 21, output plunger rod section 22 and piston member 50. In a preferred embodiment, piston member 50 is located substantially at a midpoint of said plunger member 20, thereby dividing said plunger member 20 into said input plunger rod section 21 and output rod section 22. Input plunger rod section 21 is slidably disposed in upper aperture 17 extending through top member 15, while output plunger rod section 22 is slidably disposed in lower aperture 18 extending through base member 16. Piston member 50 is slideably disposed within inner chamber 12 of housing member 13.

Piston member 50, having a substantially circular outer shape, extends radially outward from said plunger member 20. Said piston member 50 has upper surface 51, lower surface 52 and outer surface 54; said outer surface 54 defines an outer diameter that is substantially equal to the inner diameter of housing 13. As such, outer surface 54 of piston member 50 forms a fluid pressure seal against inner surface 14 of housing wall 11, thereby preventing fluid from flowing between said inner surface 14 of housing wall 11 and outer surface 54 of piston member 50. As a result, piston member 50 effectively divides inner chamber 12, into upper inner chamber section 61 and lower inner chamber section 62.

As depicted in FIG. 1, piston member 50 further comprises transfer tube 53 that extends from upper surface 51 of piston member 50 to lower surface 52 of said piston member 50. Transfer tube 53 has a fixed diameter and permits fluid communication between upper chamber section 61 and lower chamber section 62. As a result, transfer tube 53 allows for the flow or transfer of fluid(s) from upper chamber section 61 to lower chamber section 62, and vice versa.

A fluid having desired properties is disposed within inner chamber 12 of housing member 13. In certain applications, said fluid can comprise air or another gas exhibiting desired characteristics. In other applications, said fluid can comprise a liquid including, without limitation, a liquid having a desired dynamic viscosity. By way of illustration, but not limitation, said fluid can comprise glycerol, propylene glycol or other liquid having desired characteristics.

In a preferred embodiment, clevis bracket assembly 70 extends in a relatively downward direction from base member 16 of housing 13, thereby allowing dispensing assembly 100 of the present invention to hold a conventional syringe or other device that can be used to dispense a particular drug, medication or other substance. Clevis bracket assembly 70 generally comprises clevis extension member 77 having upper end 77a and lower end 77b. A pair of spaced-apart arm-like clevis bracket members 71 is disposed at or near said lower end 77b. Additionally, lip member 72 is disposed near the outer end of each clevis bracket member 71.

In a preferred embodiment, although not depicted in FIG. 1, it is to be observed that a conventional syringe can be placed and mounted within clevis bracket assembly 70 of dispensing assembly 100 of the present invention as more fully described below. When dispensing assembly 100 of the present invention is in operation, said syringe can be loaded with a particular medication, drug or other substance, for which regulated dispensing is beneficial. Dimensions of dispensing assembly 100 can be adjusted to satisfy a variety of characteristics and criteria for size, capacity and proper linear travel rate of said syringe.

FIG. 2A depicts a side, longitudinal sectional view of a preferred embodiment of dispensing assembly 100 of the present invention, as well as a detailed view of a highlighted portion of said longitudinal sectional view. As depicted in FIG. 2A, plunger member 20 is received within inner chamber 12 of housing 13, wherein plunger member 20 comprises piston member 50 that is slidably disposed within inner chamber 12 of housing member 13, and thus, effectively separating inner chamber 12 into upper chamber section 61 and lower chamber section 62.

FIG. 2B depicts a detailed view of a highlighted portion of said longitudinal sectional view of piston member 50 of the present invention. As illustrated in FIG. 2B, piston member 50 further comprises radial lip seal 80 that is located adjacent to inner surface 14 of side wall 11 of housing member 13, wherein radial lip seal 80 can act as the sealing method of piston member 50 to inner surface 14 of side wall 11.

Still referring to FIGS. 2A and 2B, in a preferred embodiment, for rapid retraction of plunger member 20, a negative or relatively upward force of input plunger rod section 21 moves piston member 50 in a relatively upward direction, thereby producing a relatively rising fluid pressure in upper chamber section 61 and a relatively decreasing fluid pressure in lower chamber section 62. The angle of radial lip seal 80 is not positioned to seal against this shift in fluid pressure. As a result, supple radial lip member 81 of radial lip seal 80 collapses and allows for the flow or transfer of fluid(s) through gap 82 between outer surface 54 of piston member 50 and inner surface 14 of housing wall 11, thereby allowing fluid to bypass seal 80, as illustrated in FIG. 2B. The retraction rate depends on the dynamic fluid viscosity versus the fluid pressure, the clearance of inner surface 14 of housing wall 11 to outer surface 54 of piston member 50, and any obstruction presented by body member 83 of radial lip seal 80 in its collapsed state. As a result, the retraction rate can be modified accordingly depending on a particular medication, drug, or other substance that is used as the fluid medium because certain medications and drugs require specific dispensing rates in order to be dispensed in a safe manner.

FIG. 3A depicts a front view of a preferred embodiment of dispensing assembly 100 of the present invention. Housing member 13 partially encloses plunger member 20, wherein input plunger rod 21 and output plunger rod 22 can slidably retract from housing 13 or can be slidably compressed and received within housing member 13. Clevis bracket assembly 70 axially extends in a relatively downward direction from base member 16 of housing 13. Clevis bracket assembly 70 generally comprises clevis extension member 77 having upper end 77a and lower end 77b. Further, clevis extension member 77 comprises front opening 73 that leads to inner channel 75, thereby allowing for placement of a conventional syringe and for output plunger rod 22 to slidably extend through inner channel 75. Additionally, clevis bracket assembly 70 comprises clevis gap 74 that is beneficially located between clevis extension member 77 and clevis bracket members 71, thereby allowing for an opening for a flange of a conventional syringe to be loaded within dispensing assembly 100.

Although not depicted in FIG. 3A, when force is applied to input plunger rod 21, the force is then transferred to output plunger rod 22, thereby allowing for output plunger rod 22 to slidably extend through inner channel 75, and thus, transfer said force to a conventional syringe. As a result, a conventional syringe can then dispense a particular medicine, drug, or other substance into a patient or an intravenous (IV) port at an appropriate rate.

FIG. 3B depicts a side, longitudinal sectional view of a preferred embodiment of dispensing assembly 100 of the present invention. As depicted in FIG. 3B, plunger member 20 is received within inner chamber 12 of housing 13, wherein plunger member 20 comprises piston member 50, thereby effectively separating inner chamber 12 into upper chamber section 61 and lower chamber section 62.

FIG. 3C depicts a detailed view of a highlighted portion of said longitudinal sectional view of piston member 50 of the present invention. As illustrated in FIG. 3C, piston member 50 comprises radial lip seal 80 that is adjacently located to inner surface 14 of side wall 11 of housing member 13.

Still referring to FIGS. 3B and 3C, in a preferred embodiment, when a force is exerted on input plunger rod 21, and is thus operationally pushed in a relatively downward direction in order to dispense a particular medication, drug, or other substance, the fluid pressure in lower chamber section 62 increases, while the fluid pressure in upper chamber section 61 simultaneously decreases. Thus, as a result, supple lip member 81 of radial lip seal 80 can be forced against inner surface 14 of cylinder wall 11, thereby beneficially creating a seal in order to stop and prevent the bypass action of fluid(s), as depicted in FIG. 3C.

FIG. 4A depicts a bottom view of a preferred embodiment of dispensing assembly 100 of the present invention. Clevis bracket assembly 70 comprises a substantially semi-circular configuration having front opening 73 disposed axially along clevis extension member 77, thereby creating channel 75 and allowing a conventional syringe to be easily placed and mounted within clevis bracket assembly 70. Pad 42 of output plunger rod 22 comprises a substantially circular configuration, wherein pad 42 of output plunger rod 22 adjacently contacts a top end of a retracted syringe plunger of a conventional syringe (although not depicted in FIG. 4A), thereby allowing for a steady and evenly dispersed pressure to be applied to said syringe when a particular medicine, drug, or other substance is being dispensed at the appropriate rate.

FIG. 4B depicts a side perspective view of a preferred embodiment of dispensing assembly 100 of the present invention. Base member 16 of housing 13 is attachably connected to semi-circular clevis bracket assembly 70, wherein clevis bracket assembly 70 comprises clevis extension member 77. Clevis extension member 77 further comprises front opening 73 in order to place and mount a conventional syringe within dispensing assembly 100 of the present invention. Input plunger rod 21 comprises a substantially cylindrical rod-like configuration having a substantially planar plate, or upper pad 31, located at a top end 33 of input plunger rod 21, thereby allowing for a user to easily press and apply force to upper pad 31 with a thumb. Output plunger rod 22 comprises a substantially cylindrical rod-like configuration having pad 42 located at a bottom end 41 of output plunger rod 22, thereby allowing for a top end of a retracted syringe plunger to contact pad 42 of output plunger 40 in order to properly hold and secure a conventional syringe in place.

Clevis bracket assembly 70 comprises clevis gap 74 disposed between clevis extension member 77 and clevis bracket members 71, wherein clevis gap 74 provides an opening for a bottom end of a flange of a conventional syringe to be received within dispensing assembly 100.

Further, clevis bracket members 71 comprise a substantially planar upper surface 76, thereby allowing for a bottom end of a flange of a syringe to rest upon said planar surface 76 when a conventional syringe is loaded and positioned into dispensing assembly 100. Additionally, clevis lip members 72 are disposed near the outer end of each clevis bracket member 71, wherein clevis lip members 72 prevent a flange of a syringe from sliding out of dispensing assembly 100 of the present invention.

Figure 5:
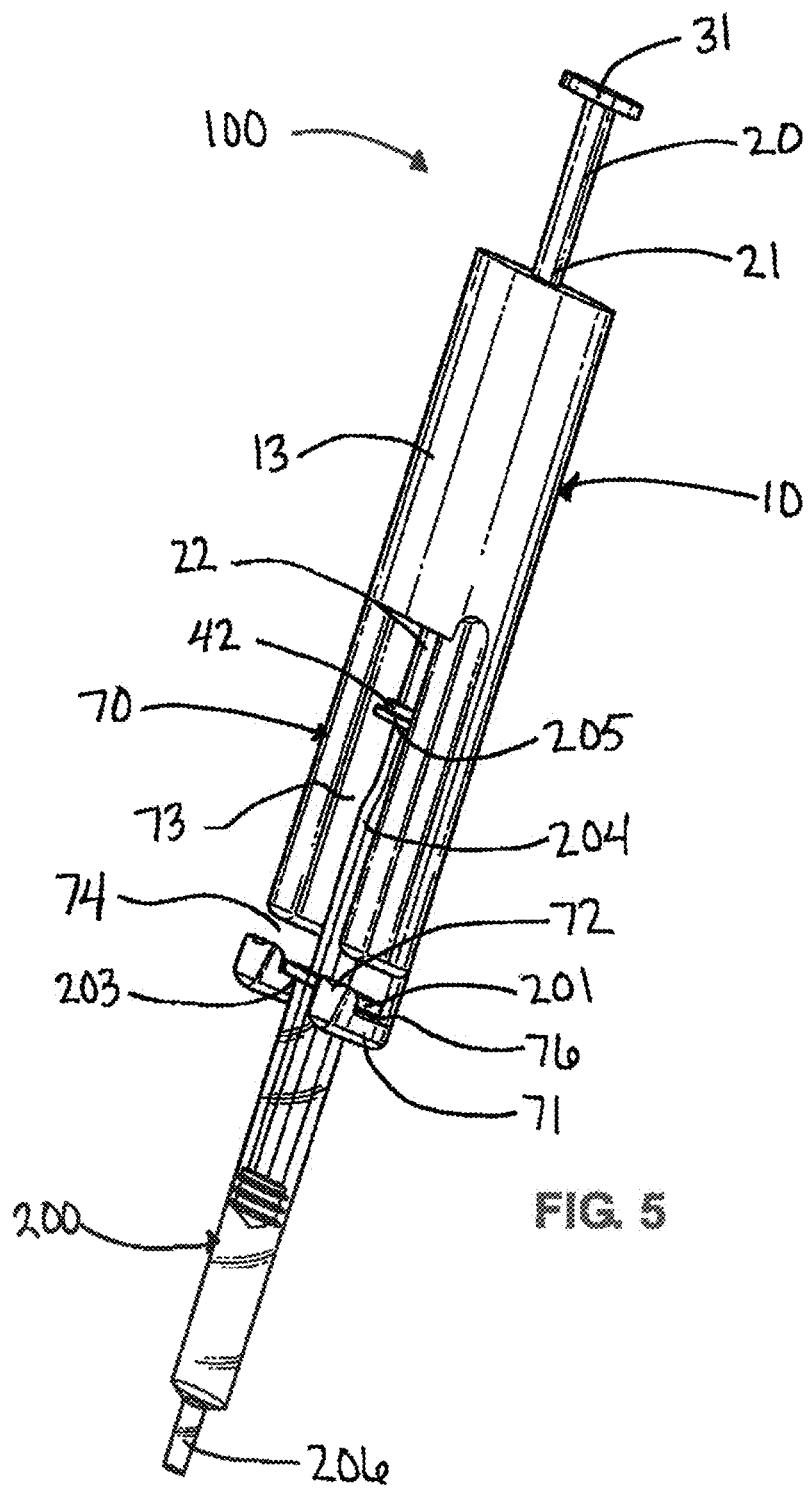
FIG. 5 depicts a side perspective view of a preferred embodiment of a syringe apparatus of the present invention comprising a conventional syringe installed within said syringe apparatus.

FIG. 5 depicts a side perspective view of a preferred embodiment of dispensing assembly 100 of the present invention comprising conventional syringe 200 loaded and mounted within the present invention. Conventional syringe 200 is loaded and inserted into dispensing assembly 100 through front opening 73 of clevis bracket assembly 70. Top end 205 of retracted syringe plunger 204 is axially aligned below pad 42 of output plunger rod 22, and thus, adjacently contacts pad 42 of output plunger rod 22, thereby beneficially holding syringe 200 in place. Bottom end 203 of flange 201 is inserted into clevis gap 74, and is thereby positioned on upper surface 76 of clevis bracket members 71. Flange 201 is securely fastened within clevis bracket assembly 70 of dispensing assembly 100 by way of clevis lip members 72, wherein clevis lip members 72 assist in keeping flange 201 latched within dispensing assembly 100 of the present invention.

Syringe 200 is loaded into dispensing assembly 100 of the present invention by inserting flange 201 of syringe 200 at a top surface of a barrel into clevis gap 74. Once any clearance is taken up between pad 42 at the lower distal end of output plunger rod section 22 of dispensing assembly 100 of the present invention and input plunger 204 of syringe 200, dispensing of any medicine, drug or substance in said syringe 200 can begin.

Further, although not illustrated in FIG. 5, an operator can optionally connect a syringe output 206 to an intravenous (IV) port. With fingers wrapped around housing 13 of dashpot member 10 and thumb placed atop upper pad 31 of input plunger rod section 21, the operator can then apply a steady downward force and verify that a particular medicine, drug or other substance, within syringe 200 is being dispensed at a desired rate. This is necessary because particular medications, drugs, or other substances require a specific dispensing rate in order to be safely administered. The force applied to input plunger rod section 21 is transmitted to piston member 50 and then transferred through to output plunger rod section 22, and thus to syringe plunger 204. As a result, the medicine, drug, or other substance can be appropriately dispensed to a patient or other recipient or device at a desired flow rate.

As piston member 50 moves in a relatively downward direction, the fluid pressure in upper chamber section 61 decreases while the fluid pressure in lower chamber section 62 simultaneously increases. As a result, fluid is trapped within lower chamber section 62, such that it can only "escape" via transfer tube 53; in this manner, progress of piston member 50 in the downward direction is limited. Thus, transfer tube 53 allows for the flow or transfer of fluid(s) from upper chamber section 61 to lower chamber section 62 in order to control a maximum effective rate of travel of plunger member 20 and piston member 50 over a specified range of input pressures. The linear plunger member travel rate is thus directly proportional to a syringe fluid medium discharge flow rate. The rate of transfer of such fluid through transfer tube 53 (and, thus, speed of travel of piston 50) can be adjusted by varying the dimensions (diameter and/or length) of transfer tube 53, the dynamic viscosity and compressibility of the fluid, and by the input force exerted on plunger 20.

Figure 6:
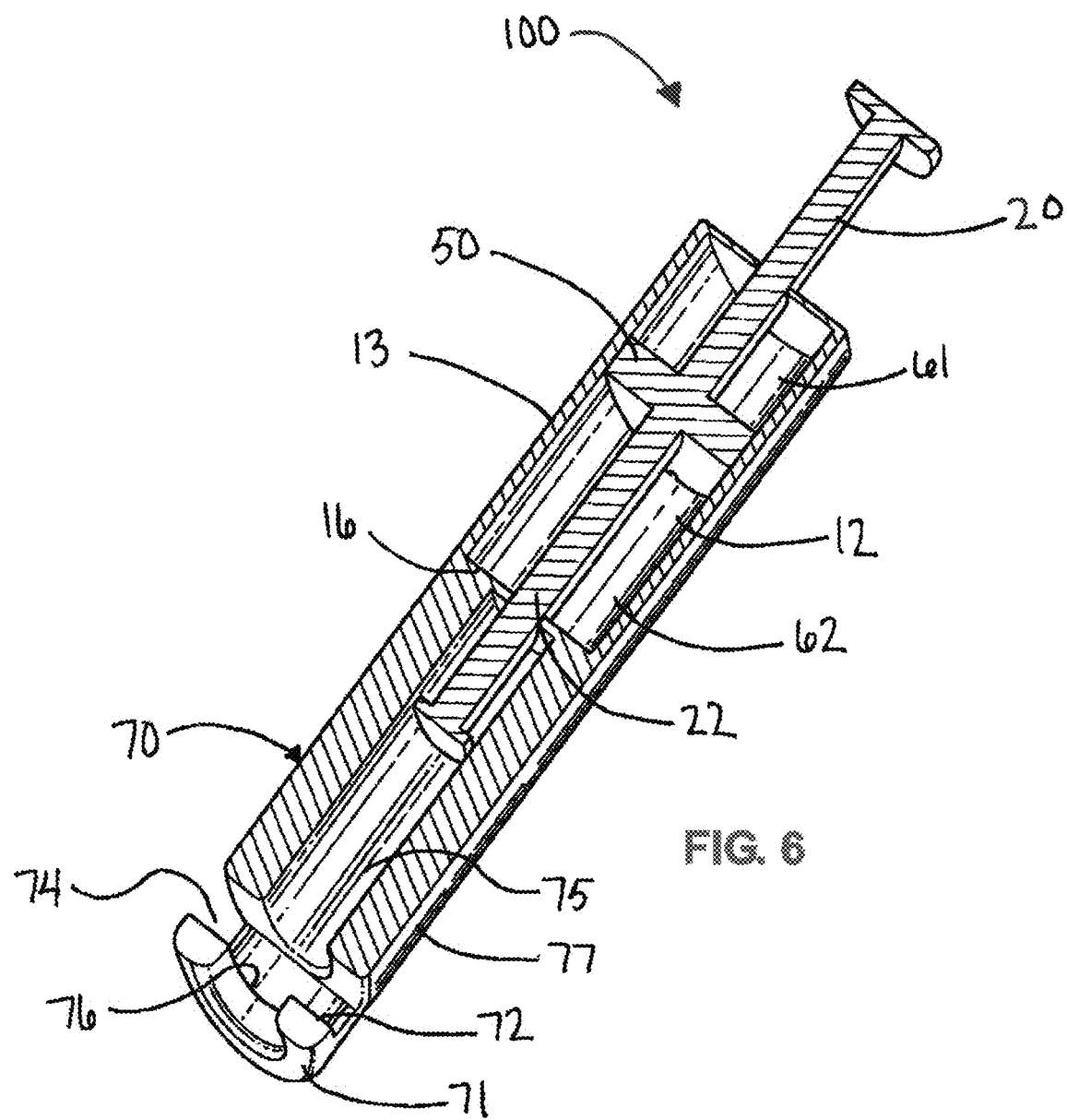
FIG. 6 depicts a perspective, longitudinal sectional view of a preferred embodiment of a syringe apparatus of the present invention.

FIG. 6 depicts a perspective, longitudinal sectional view of a preferred embodiment of dispensing assembly 100 of the present invention. Plunger member 20 is partially disposed within inner cavity 12 of housing member 13, wherein piston member 50 effectively divides inner cavity 12 into upper chamber section 61 and lower chamber section 62.

As depicted in FIG. 6, clevis bracket assembly 70 is attachably connected and axially disposed in a relatively vertical direction to base member 16 of housing member 13, wherein clevis bracket assembly 70 comprises inner channel 75 to allow for output plunger rod 22 and a conventional syringe to slidably extend and retract along inner channel 75 as dispensing assembly 100 of the present invention is in operation. Clevis bracket assembly 70 comprises clevis gap 74 that is disposed between clevis extension member 77 and clevis bracket members 71, thereby allow for an opening in order to place a flange of a conventional syringe within clevis bracket assembly 70 and position said flange atop upper surface 76 of clevis bracket members 71, whereby clevis lip members 72 can securely hold said conventional syringe within dispensing assembly 100 of the present invention (and prevent slippage out of clevis bracket members 71).

Figure 7:
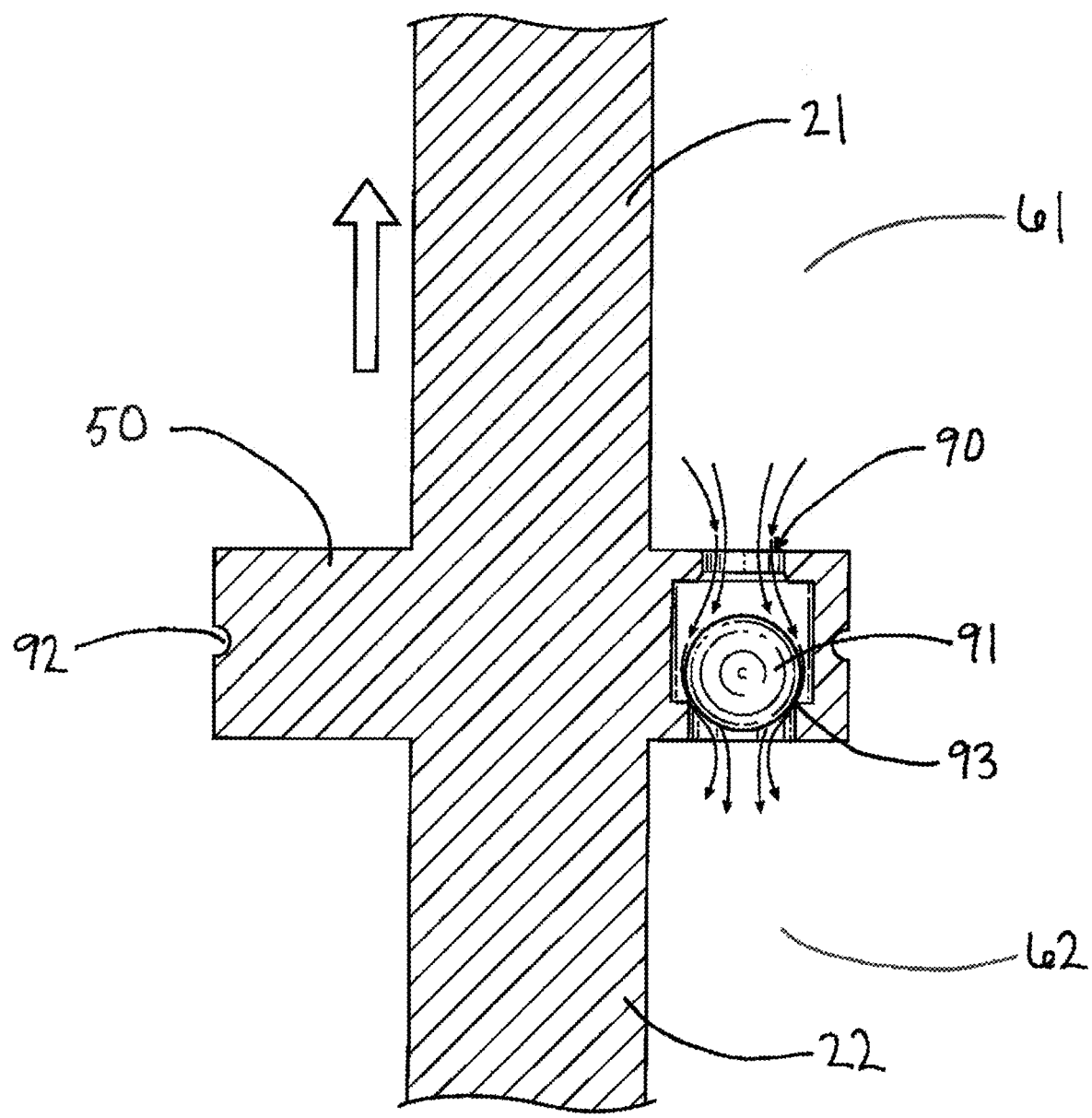
FIG. 7 depicts a side, longitudinal sectional view of an alternative embodiment of a piston member comprising a ball check valve.

FIG. 7 depicts a side, longitudinal sectional view of an alternative embodiment of piston member 50 comprising ball check valve 90. Ball check valve 90 comprises an alternate sealing mechanism that can be used within piston member 50 of dispensing assembly 100. Although not depicted in FIG. 7, in operation, piston member 50 is sealed against inner surface 14 of cylinder wall 11 of housing member 13 with an O-ring located in a notch, or a landing 92.

As illustrated in FIG. 7, when input plunger rod section 21, and thus piston member 50 are retracted in a substantially upward direction, the fluid flow of the medicine, drug, or other substance can act on check ball 91, thereby forcing check ball 91 in a relatively downward direction against a plurality of ball retainers 93. The fluid can then flow around a relief port (not depicted in FIG. 7) into lower chamber section 62 at a relatively high rate, thereby allowing for rapid retraction.

Figure 8:
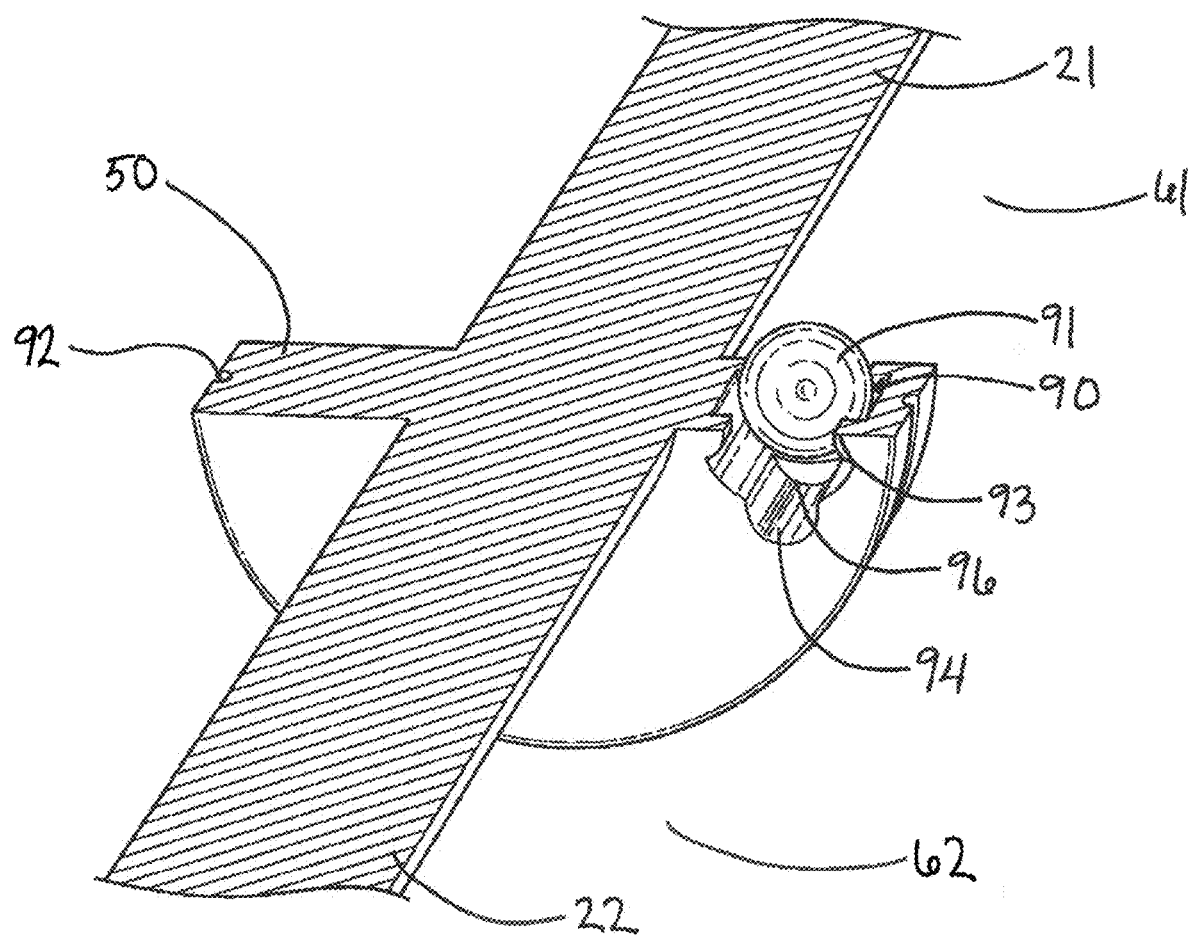
FIG. 8 depicts a perspective, longitudinal sectional view of an alternative embodiment of a piston member comprising a ball check valve.

FIG. 8 depicts a perspective, longitudinal sectional view of an alternative embodiment of piston member 50 comprising ball check valve 90. Although not depicted in FIG. 8, piston member 50 is sealed against inner surface 14 of cylinder wall 11 by way of an O-ring located in notch 92.

As illustrated in FIG. 8, as input plunger rod section 21, and thus piston member 50 are retracted in a relatively upward direction, the fluid pressure of the medicine, drug, or other substance can act upon check ball 91, thereby forcing it in a relatively downward direction against ball retainer(s) 93. The fluid can then flow around relief port 94. Relief port 94 comprises a channel 96, or a passage, that is exposed when check ball 91 is forced against ball retainer(s) 93 by the fluid pressure, thereby allowing the fluid to flow into lower chamber section 62 at a relatively high rate, and thus, allowing for rapid retraction.

Figure 9:
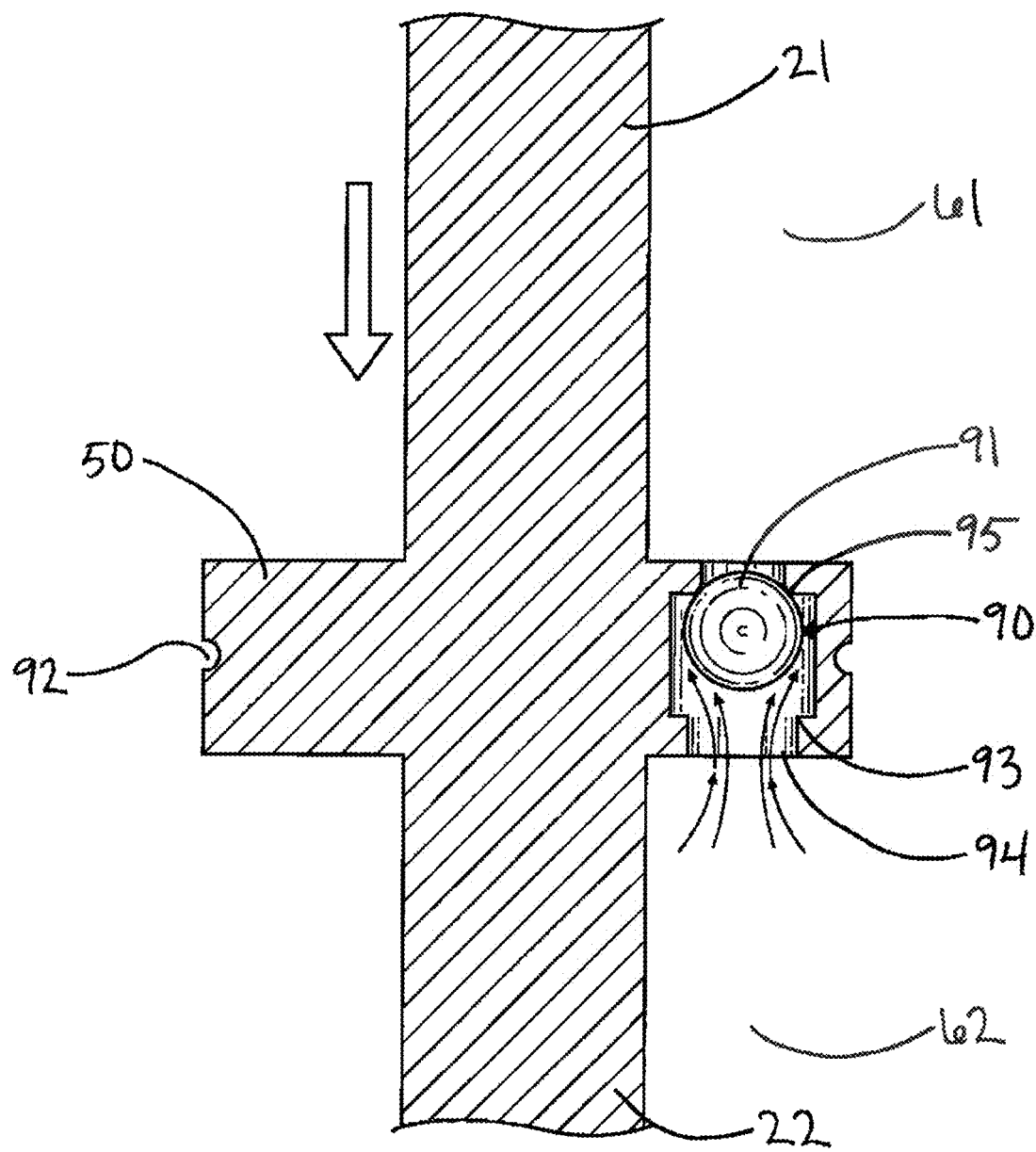
FIG. 9 depicts a side, longitudinal sectional view of an alternative embodiment of a piston member comprising a ball check valve.

FIG. 9 depicts a side, longitudinal sectional view of an alternative embodiment of piston member 50 comprising ball check valve 90. As illustrated in FIG. 9, when the direction of piston member 50 is reversed, and input plunger rod section 21 is thus, compressed in order to dispense fluid, the fluid reverses direction, and the fluid pressure simultaneously lifts check ball 91 in a relatively upward direction until it contacts a sealing seat 95, thereby creating a seal in order to stop and prevent the flow of fluid. At this point, the travel rate of piston member 50 is now controlled by the transfer tube 53 (although not depicted in FIG. 9).

FIG. 10 depicts a tabular chart illustrating a variety of medications and concentrations thereof with proposed injection rates. FIG. 10 illustrates how different medications require different proposed injection rates depending on a variety of factors, including, but not limited to, the concentration of each medication and the dosage amount of each medication that is to be dispensed and administered. Different injection rates are generally required for different medications, drugs, or other substances in order to be properly and safely administered. As a result, the dispensing assembly of the present invention can be locked into a specific retraction rate in order to properly accommodate the particular injection rate of a particular medication, drug, or other substance that is to be used.

Figure 11:
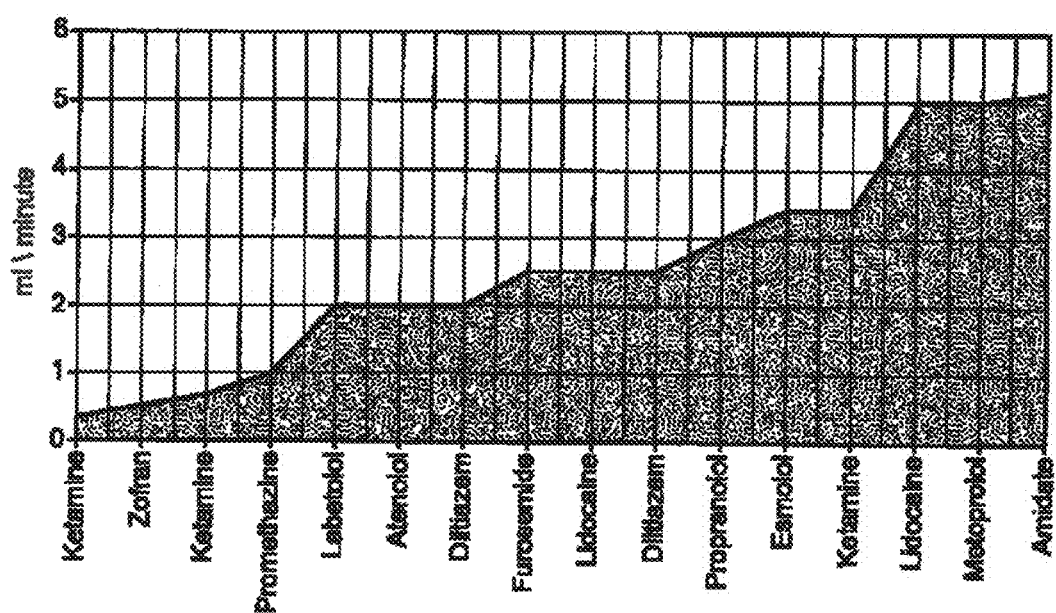
FIG. 11 depicts a graphical representation illustrating proposed injection rates for a variety of different medications.

FIG. 11 depicts a graphical illustration reflecting injection rates for a variety of medications. As illustrated in FIG. 11, a variety of known medications are listed along an "X" axis, with a "Y" axis representing a proposed injection rate in milliliters per minute (ml/minute). Each particular medication has its own proposed injection rate, which is thereby graphed along the grid. Thus, the grid displays the proposed injection rates in ml/minute for each medication that is listed along the "X" axis. As a result, each medication varies in an approximate range of 0.3 ml/minute to 5.2 ml/minute in its proposed injection rate in order to be administered properly and safely.

Figure 12:
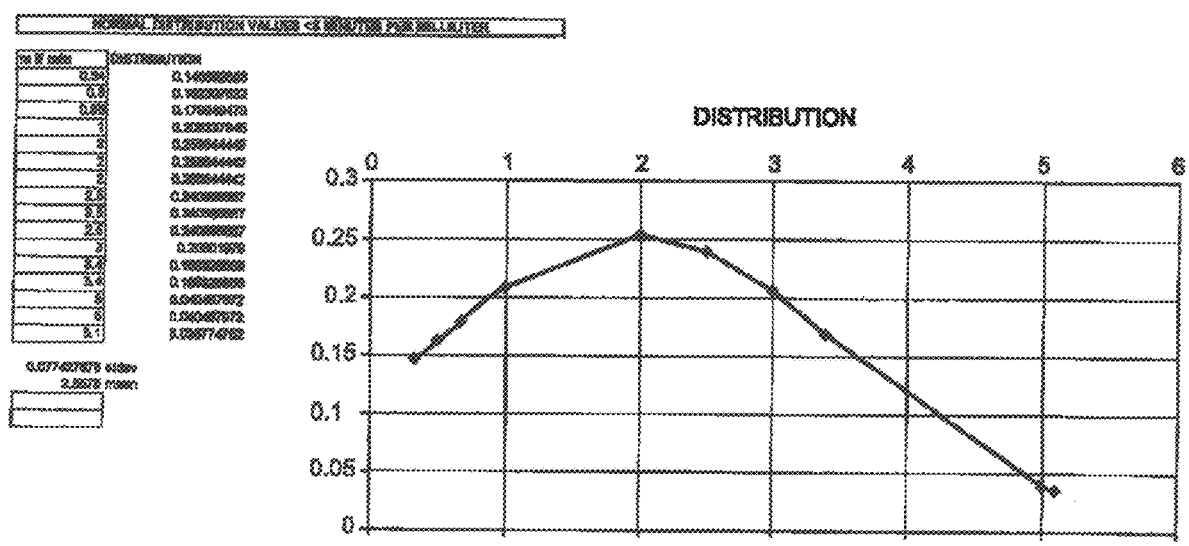
FIG. 12 depicts a graphical representation of a distribution chart illustrating injection rates for a variety of medications.

FIG. 12 depicts a graphical illustration of a distribution chart depicting injection rates for a variety of medications. The proposed injection rates in ml/minute of each medication previously listed in FIGS. 10 and 11 are then converted into normal distribution values. As depicted in FIG. 12, the normal distribution values of each medication previously listed in FIGS. 10 and 11 are then graphed along a distribution grid, thereby illustrating a standard bell curve having a standard deviation of approximately 0.077427878 and a mean distribution value of approximately 2.5575.

The above-described invention has a number of particular features that should preferably be employed in combination, although each is useful separately without departure from the scope of the invention. While the preferred embodiment of the present invention is shown and described herein, it will be understood that the invention may be embodied otherwise than herein specifically illustrated or described, and that certain changes in form and arrangement of parts and the specific manner of practicing the invention may be made within the underlying idea or principles of the invention.

What is claimed:

1. A syringe dispensing assembly for controlling a fluid dispensing rate of a syringe comprising:
   a) a housing defining a top, a base having an aperture, and an inner chamber between said top and said base;
   b) a first plunger having a top and a bottom, wherein said first plunger is slidably disposed through said housing and said aperture in said base of said housing, and wherein said bottom of said first plunger extends from said base of said housing;
   c) a piston operationally attached to said first plunger, wherein said piston is slidably disposed within said inner chamber of said housing and separates said housing into an upper inner chamber section and a lower inner chamber section, and wherein said piston has a transfer tube extending through said piston from said upper inner chamber section to said lower inner chamber section;
d) a first fluid disposed in said housing;
e) a check valve disposed in said piston, wherein said check valve is configured to permit said first fluid to flow from said upper inner chamber section to said lower inner chamber section, and to prevent said first fluid from flowing from said lower inner chamber section to said upper inner chamber section;
f) a clevis bracket assembly further comprising:
 i) a clevis extension member having a top and a bottom, wherein said top of the clevis extension member is operationally attached to said housing;
 ii) a clevis bracket disposed at said bottom of said extension member; and
g) the syringe comprising a barrel having an outlet, a syringe plunger slidably disposed in said barrel, and a flange connected to said barrel, wherein said barrel contains a second fluid, said flange is received on said clevis bracket, said first plunger is adapted to apply axial force to said syringe plunger in order to dispense said second fluid from said outlet of said barrel and said first and second fluids remain separated from each other at all times.

2. The syringe dispensing assembly of claim 1, wherein an axial force applied to said top of said first plunger is transferred to said bottom of said first plunger.

3. The syringe dispensing assembly of claim 1, wherein said first fluid comprises a gas.

4. The syringe dispensing assembly of claim 1, wherein said first fluid comprises a substantially incompressible liquid.

5. The syringe dispensing assembly of claim 4, wherein said substantially incompressible liquid comprises glycerol or propylene glycol.

* * * * *